United States Patent [19]

Schmitt et al.

[11] 4,131,729

[45] Dec. 26, 1978

[54] DENTAL COMPOSITIONS COMPRISING ACRYLIC ESTERS OF TRICYCLO [5.2.1.0$^{2,6}$] DECANE POLYMERS

[75] Inventors: Werner Schmitt; Robert Purrmann, both of Starnberg, Obb.; Peter Jochum; Wolf-Dietrich Zahler, both of Hechendorf, all of Fed. Rep. of Germany

[73] Assignee: ESPE Fabrik Pharmazeutischer Präparate GmbH, Fed. Rep. of Germany

[21] Appl. No.: 898,680

[22] Filed: Apr. 21, 1978

[51] Int. Cl.$^2$ .................... C08F 32/08; C08F 132/08; C08F 122/10; C08F 4/34
[52] U.S. Cl. .............................. 526/282; 204/159.23; 260/42.15; 260/42.18; 260/885; 260/DIG. 36; 526/227; 526/231
[58] Field of Search .............. 526/282; 260/DIG. 36; 204/159.23

[56] References Cited

U.S. PATENT DOCUMENTS

| | | | |
|---|---|---|---|
| 2,454,743 | 11/1948 | Mowry et al. | 526/282 |
| 3,923,740 | 12/1975 | Schmitt et al. | 526/326 |

*Primary Examiner*—Herbert J. Lilling
*Attorney, Agent, or Firm*—Burns, Doane, Swecker & Mathis

[57] ABSTRACT

An improved dental composition having shortened hardening time and after hardening increased compressive strength and abrasion resistance, including a radical-inducing compound and a polymerizable acrylic or methacrylic acid ester or diester compound with at least 20 percent by weight of the polymerizable compound being the diacrylic or dimethacrylic acid ester of bishydroxymethyltricyclo [5.2.1.0$^{2,6}$]-decane. Other monofunctional or difunctional acrylic or methacrylic acid esters as well as fillers, pigments and stabilizers can be included.

12 Claims, No Drawings

DENTAL COMPOSITIONS COMPRISING ACRYLIC ESTERS OF TRICYCLO [5.2.1.0$^{2,6}$] DECANE POLYMERS

It is well known that dental compositions which contain polymerizable monomers which are to be used for the filling of teeth and for dentures can be hardened by a polymerization reaction induced by radicals. Esters of acrylic acid and methacrylic acid are monomers which are suitable for these purposes. If bifunctional acrylic acid esters are employed in such polymerization reactions, three-dimensional, crosslinked masses of great hardness and abrasion resistance are obtained. U.S. Pat. No. 3,066,112 describes the use of one dimethacrylic acid ester, derived from bisphenol A and obtainable by its reaction with glycidylmethacrylate, to be used specifically for the preparation of tooth fillings. Similar products, which however are free of any hydroxyl groups, are described by British Pat. No. 1,267,564 and U.S. Pat. No. 3,923,740 which are identical with German Pat. No. 1,921,869. The polymers obtained by means of these substances have the advantage that they will remain dimensionally stable even in the presence of water due to the absence of the hydroxyl groups which is in contrast to the masses described by U.S. Pat. No. 3,066,112 which, being produced by the addition of the bisphenol A to the epoxy-group of the glycidylmethacrylate, contain two hydroxyl groups per molecule of the dimethacrylic acid compound.

These known bifunctional methacrylic acid esters are utilized in combination with radical-forming polymerization catalysts or initiators, especially in dentistry as masses or compositions for the filling of teeth and represent a definite improvement when compared with the previously used methylmethacrylates. They will polymerize quickly and thoroughly without residual monomers and have a lesser contraction at polymerization which is a main advantage. The hardened material possesses a high compressive strength as reported in the papers written by Henry L. Lee et al in J. Dent. Res. 48, pages 526 to 535 (1969) and by H. Durner in "Zahnaerztliche Welt/Reform", 81, page 764 (1972).

However, these masses obtained by the use of known bifunctional methacrylic esters, in spite of the relatively great strength of the fillings and dentures, still do not meet all dental requirements. Tooth fillings and dentures are subjected in the course of their use to an enormous chewing pressure and to wear by abrasion. It is for this reason that many dentists, in spite of the availability of these preparations, are still using amalgam for the filling of teeth although this latter material is deficient in esthetic respect and there are some objections to its use in view of its mercury content. Attempts have been made by the admixture of fillers, especially powdered silica or fine amorphous silicic acid, to improve still further the strength and abrasion characteristics of the polymerized masses. Such attempts, also including the use of tri- and tetra-functional methacrylic acid esters, were proposed by the published German applications 24 05 578, 24 32 013 and 24 38 411. However, the resulting products were not satisfactory.

The compressive strength values attained at the present time are in the general range of 2,200 to 2,900 kg/cm$^2$. Such products are acceptable in many instances but there is still a desire for tooth fillings and dentures of even greater strength and resistance to abrasion which are based on easily obtainable raw materials which can then be rapidly polymerized by the use of standard polymerization catalysts and initiators and which will fully harden within a short period of time, even without any increase in temperature.

In one embodiment, the present invention provides a dental composition, especially for tooth fillings and dentures, including at least two components, one component comprising a polymerizable diacrylic acid ester selected from the group consisting of the diacrylic acid ester or dimethacrylic acid ester of bishydroxymethyltricyclo [5.2.1.0$^{2,6}$]-decane and mixtures thereof, the other component comprising a radical-forming substance. The term "radical-forming substance" will be understood to include a compound which will form radicals under irradiation by light.

In another embodiment, the present invention provides a method for forming dental fillings and prosthetic dental appliances in which a polymerizable diacrylic or dimethacrylic acid ester is polymerized to form a hardened product, the improvement wherein at least 20 percent by weight of said polymerizable ester is the ester of bishydroxymethyltricyclo[5.2.1.0$^{2,6}$]-decane.

In still another embodiment, the present invention provides an improved dental composition having shortened hardening time and after hardening increased compressive strength and abrasion resistance comprising a polymerizable acrylic or methacrylic acid ester or diester and a radical-forming compound, at least 20 percent of the polymerizable ester being the diacrylic or dimethacrylic acid ester of bishydroxymethyltricyclo [5.2.1.0$^{2,6}$]-decane.

It has been found unexpectedly and surprisingly that diacrylic or dimethacrylic acid esters of bishydroxymethyltricyclo [5.2.1.0$^{2,6}$]-decane are particularly suitable polymerizable components for dental materials and will lead to dimensionally stable and hard polymerization products. The diacrylic or dimethacrylic acid ester compounds can be produced easily by esterifying dihydroxymethyltricyclodecane with acrylic or methacrylic acid or a derivative thereof by means of standard processes.

Dihydroxymethyltricyclo [5.2.1.0$^{2,6}$]-decane is commercially available and can be expressed by the following structural formula

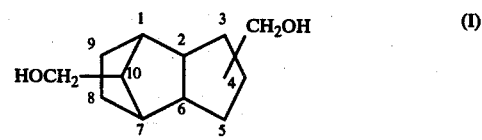

As a result of the standard processes used for the preparation of this tricyclodecane derivative, the hydroxymethyl radicals can be in the 3- and 4-position as well as in the 9- and 8-position of the tricyclodecane molecule. The commercially available product, described for example in the published German patent application No. 1,618,384, normally will contain these isomeric compounds. The published German application No. 1,694,868 describes the use of such compounds for the manufacturing of polyadducts based on triglycidylisocyanurate.

The bifunctional bisacrylic acid esters or bismethacrylic acid esters of the dihydroxymethyltricyclodecane are compounds expressed by the general formula

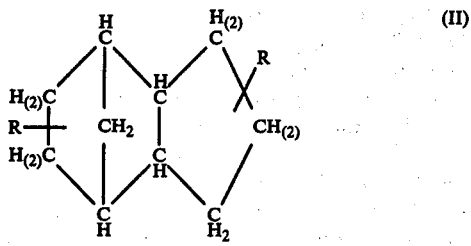

where R represents the methylene acrylate radical of the formula

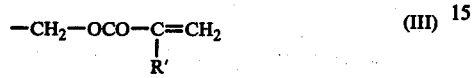

and where R' can be either H or CH$_3$.

In the general formula (II), the symbol CH$_{(2)}$ is meant to indicate that two H-atoms are present at this C-atom of the isomeric compound if the radical R is not present there.

There esters can be easily prepared in accordance with conventional methods by esterifying the dihydroxymethyltricyclodecane with the free acrylic acids in the presence of suitable catalysts, or by trans-esterification and the use of acrylic acid esters of lower alcohols, for example methacrylic acid methylester. By the admixture of polymerization inhibitors, such as p-methoxyphenol, during esterification or trans-esterification, undesirable polymerization at higher temperatures can thus be prevented in known manner.

The bifunctional acrylic esters of formula (II) are colorless, very fluid oils which due to their viscosity (which is relatively low in comparison with the bifunctional methacrylic acid esters used heretofore in dentistry), can be processed very readily. The compositions prepared in accordance with the present invention can contain known radical-producing substances used for such polymerization purposes and in the same amounts as generally used for such purposes. Suitable polymerization catalysts are, among other substances, peroxide or azo-compounds, especially lauroyl peroxide, chlorobenzoyl peroxide and the like. For fields of application requiring rapid polymerization at room temperature, especially in the case of materials used for the filling of teeth, the known oxidation-reduction systems are preferably used, which systems usually consist of one peroxide and one reducing agent. The reducing agent can be, for example, amines, sulphinic acids, substituted sulphones, so-called CH-active compounds such as barbituric acids or β-diketones. Non-discoloring redox-systems are preferably used. If amine-containing redox-systems are employed, amines should be selected which are relatively stable with respect to discoloring, especially N,N-bishydroxyalkyl-3,5-xylidines or N,N-bishydroxyalkyl-3,5-di-t-butylanilines.

If compounds are present which will initiate polymerization when subjected to visible or ultra-violet light, it becomes possible to attain a rapid polymerization by irradiation, a particularly advantageous feature for many purposes.

Compositions containing suitable UV-initiators are very stable in the dark and the substances proposed by the invention will therefore permit the manufacture of single-unit preparations which are ready for use. For this purpose, a conventional initiator for ultra-violet polymerization, for example, benzoin, benzoin ether, α-substituted benzoins or benzoin ethers, benzil, benzilketals, halogeneous aromatic compounds such as halogenmethylated benzophenones and the like is dissolved in the bifunctional esters. The admixture of small quantities of organic phosphites will lead to an even greater acceleration of rapidly progressing polymerization by ultra-violet light.

Single-unit preparations containing polymerization initiators which react to visible light can be hardened with particular ease. Initiators of this type are, for example, combinations of quinones and aliphatic amines, or combinations of benzilketals, benzophenones or quinones with amines. Preparations containing such initiator systems are sufficiently stable in the dark and allow sufficient time for processing under daylight or other light of usual intensity. However, polymerization will be rapid if the substance is subjected to an intensive visible irradiation furnished by a special light source.

The bifunctional esters of the present invention are designed for materials to be used in the dental field which includes tooth fillers as well as preparations for building up portions of a tooth, coating and sealing masses, priming materials for cavities, materials for jackets, bridges and facings, masses for the manufacture of artificial teeth, materials for prosthetic devices as well as orthodontic devices. In practice, these materials can be utilized in all cases where synthetic or polymerizable materials are normally used in the dental field.

The substances can be used either as two-component systems, for example, as preparations consisting of one unit containing the monomer and one filling-material unit which contains the polymerizations catalyst, or in the form of two liquid components or two paste components, with the two components of redox-systems distributed among the two units. It is also possible to prepare the substances proposed by the invention in a preapportioned form, that is, in plastic containers where the components are originally kept separately and where a mechanical mixing process will occur when the two components are combined with each other. Another advantageous use is possible in the polymerization of tooth-filling and sealing masses initiated by ultra-violet or visible light, where the masses are furnished, preferably in the form of single units ready for use.

The bifunctional methacrylic acid esters which are used in accordance with the present invention result in an increase in the strength of the materials in comparison with materials used heretofore. It is possible, for example, to raise the compressive strength of tooth fillings, accomplished with standard paste-paste preparations, from approximately 2,500 kg/cm$^2$ to approximately 4,000 kg/cm$^2$ simply by replacing the known bifunctional methacrylic esters with the esters proposed by the present invention. Furthermore, the hardening will then also be greatly accelerated. If standard redox-systems are being used, the time elapsing from the start of the gelling up to the final hardening will be reduced to one-half or even one-fourth of the conventional time without any change in the processing time (that is, the time up to the start of the polymerization). This feature is particularly important in case of preparations which are applied inside the mouth, especially when tooth fillings are being inserted.

The bifunctional esters used in accordance with the present invention can be mixed with conventional monofunctional acrylic esters and methacrylic esters.

They can also be utilized in conjunction with known bifunctional methacrylic esters. For example, an admixture of bifunctional esters disclosed by British Pat. No. 1,267,564, U.S. Pat. No. 3,923,740 or German Pat. No. 1,921,869, which are free of hydroxyl groups, can be used to define a specific refractive index, or the co-use of esters which were disclosed by U.S. Pat. No. 3,066,122 and which do contain hydroxyl groups, can serve to define a low but specifically desired water absorption by the polymerization products which in many cases is expedient in order to avoid marginal leaking of tooth fillings. The combinations of the substances proposed by the invention with these known monomeric diacrylates or alkanedioldiacrylates result surprisingly in polymerization products possessing a strength which is only slightly lower and in some instances even greater than the strength of the substances of the invention employed without any admixture. Such mixtures should contain at least 20 percent of the particular tricyclodecane monomers proposed by the invention, based on the total polymerizable monomeric content of the composition. Known bifunctional monomers which are particularly suitable for this novel combination with the monomeric compounds of the invention are the diacrylate or dimethacrylate of hexanediol, bis-(p-hydroxyethoxy-)-phenylpropane or of bis-[p-($\gamma$-hydroxypropoxy)-phenyl]-propane. On the basis of such combintions, it becomes possible to create particularly high-grade dental preparations, especially compositions for the filling and sealing of teeth, either on a paste/paste basis or in the form of single-unit systems. In the case of the first-mentioned method, one paste can contain a tricyclodecane monomer substance proposed by the invention, and the other a known monomeric substance; if the redox catalyst system is used, one paste will contain the peroxide and the other paste the activator. The single-unit systems comprise mixtures of the diacrylates proposed by the invention and known monomers such as hexanedioldimethacrylate. After the mixture of the two pastes (or after irradiation of the compositions which contain polymerization activators responsive to light), hardening will occur, resulting in polymerization products with superior strength characteristics.

The use of conventional fillers is possible and effective. Especially suitable are quartz and quartz glass, as well as other glasses, for example, glasses having aluminosilicate bases, and glasses which will provide the dental materials with some opacity to X-rays, such as barium and lanthanum glasses. These inorganic fillers are silanized in a known manner. The same applies to fibers, for example, quartz or glass fibers, which can be admixed to improve the mechanical characteristics of the materials. Insoluble inorganic salts or minerals, for example, calcium fluoride, can also be used as fillers. The exclusive or additional use of micro-fine fillers, especially amorphous $SiO_2$ or $Al_2O_3$, with particle sizes ranging from $10^{-4}$ to $10^{-6}$ mm, can also lead to advantageous results, especially for the stabilization of viscosity.

The admixture of organic polymers, generally used for dental medicine and technology, especially in connection with the manufacture of dentures and teeth, is also feasible. Particularly applicable are the polymethacrylic esters, usually available in pearl-form and tinted to match the color of the teeth. Obviously, conventional pigments, soluble dyes and so-called brighteners, used to produce a white fluorescence, etc. can also be admixed with the materials proposed by the invention.

In order to prevent premature polymerization, it will be expedient to admix antioxidants, especially of the phenolic type, for example, p-methoxyphenol, hydroquinone or 2,6-di-t-butyl-p-cresol, into the composition of the present invention. The compositions can also contain UV-absorbing stabilizers to prevent discoloration caused by light, for example derivatives of benzotriazoles, benzophenones or benzoic acid phenyl esters. The latter admixtures are especially useful for preparations which are not polymerized by ultra-violet light.

The various additional ingredients such as UV-initiators, fillers, pigments, antioxidants and the like described above are utilized in the composition of the present invention in amounts corresponding to those generally utilized for such materials in compositions according to the present state of the art.

The invention is additionally illustrated in connection with the following Examples which are to be considered as illustrative of the present invention. It should be understood, however, that the invention is not limited to the specific details of the Examples. In these Examples, the bis-hydroxymethyltricyclo-[$5.2.1.0^{2,6}$]-decane is referred to as T-diol, and its diacrylic acid and dimethacrylic acid esters as T-diacrylate or T-dimethacrylate, respectively.

EXAMPLE 1

(Preparation of the bifunctional methacrylester of the T-diol)

98 grams of T-diol, 129 grams of methacrylic acid and 200 ml of cyclohexane are heated in the presence of 7 grams of p-toluenesulphonic acid and 0.3 grams of picric acid for 24 hours while the water is distilled off. The reaction product is then rinsed repeatedly with a 2N-caustic soda solution and water and decolorized by treating it with $Al_2O_3$. 10 mgrams of p-methoxyphenol are admixed as a stabilizer to prevent premature polymerization, and the cyclohexane, used as solvent, is removed by evacuation.

The reaction yields 124 grams of dimethacrylate ester in the form of an almost colorless, very fluid oil having the following properties:

| | |
|---|---|
| Viscosity at 25° C | 1.1 P |
| $n_D^{20}$ | 1.5008 |
| Double bond equivalent | 170; 169 |

EXAMPLE 2

(Preparation of the bifunctional acrylic ester of the T-diol)

196 grams of T-diol, 216 grams of acrylic acid and 400 ml of hexane are heated in the presence of 14 grams of p-toluenesulphonic acid and 0.7 gram of picric acid for six hours while the water is distilled off. After processing as described in Example 1, there are obtained 171 grams of a colorless oil with the following properties:

| | |
|---|---|
| Viscosity at 25° C | 1.2 P |
| $n_D^{20}$ | 1.5040 |
| Double bond equivalent | 155; 158 |

EXAMPLE 3

(Preparation of an acrylic-methacrylic mixed ester of the T-diol)

59 grams of T-diol, 22 grams of acrylic acid, 52 grams of methacrylic acid, 100 ml of cyclohexane, 4 grams of p-toluenesulphonic acid and 0.16 grams of picric acid are together heated and the reaction mixture is processed as described in Example 1. There are obtained 71 grams of a colorless oil with the following properties:

| | |
|---|---|
| Viscosity at 25° C | 1.2 P |
| $n_D^{20}$ | 1.5020 |
| Double bond equivalent | 168; 172 |

Approximately 40% of the ester groups of the resulting product are acrylic acid radicals.

EXAMPLE 4

(Comparative Test, polymerization by heat)

For this comparative test, known product used is a dimethacrylate derived from bisphenol-A, produced in accordance with the example 10 of German Pat. No. 1,921,869.

In order to determine the compressive strength of the ultimate polymerization products, the known dimethacrylate as well as the T-dimethacrylate of the invention (formed in a manner as in Example 1) are each mixed with 0.6% of lauroyl peroxide, the two solutions are filled into ten cylindrical forms, each form possessing a diameter of 4 mm and a height of 8 mm, and heated, at a temperature of 130° C for 30 minutes.

The following average values for compressive strength are found when the test specimens are measured:

| | |
|---|---|
| Product according to the present invention | 1,720 kg/cm$^2$ |
| Product according to example 10 of German Patent 1,921,869 | 1,150 kg/cm$^2$ |

EXAMPLE 5

(Comparative Test, oxidation-reduction polymerization)

Two solutions are prepared containing the same amount of T-dimethacrylate. Dissolved in one solution is 0.8% of N,N-bis-hydroxyethyl-3,5-di-t-butylaniline and dissolved in the other solution is 1.0% of p-chlorobenzoyl peroxide. After mixing of equal parts of the resulting solutions, forms are filled in the same manner as described in Example 4. A hard, transparent polymerization product is obtained after a few minutes.

In the same manner, there are prepared similar solutions from the dimethacrylate of 2,2,-bis-[p-(γ-hydroxypropoxy)-phenyl]-propane, the synthesis of which is described in German Pat. No. 1,921,869. These solutions are processed to form specimen of like dimensions.

The specimens are stored for 24 hours at 36° C. The following data are then found for the average compressive strength:

| | |
|---|---|
| Product according to the present invention | 1,640 kg/cm$^2$ |
| Product of the present state of the art | 1,160 kg/cm$^2$ |

EXAMPLE 6

(Paste/paste preparation for tooth fillings)

Two pastes (denominated "A" and "B") are prepared by kneading together the following:

Paste A)
- 2,4 grams of N,N-bishydroxyethyl-3,5-di-t-butylaniline, dissolved in 300 grams of T-dimethylacrylate
- 1.8 grams of amorphous, silanized SiO$_2$ with an average primary particle size of 12 mµ and 990 grams of silanized quartz powder (<60 µm) tinted to match the tooth color Paste B)
- 300 grams of T-dimethacrylate
- 1.8 grams of the SiO$_2$ as used in Paste A
- 990 grams of silanized quartz powder (<60 µm) tinted to match the tooth color and containing 6.0 grams of p-chlorobenzoyl peroxide.

When equal parts of the two pastes A and B are mixed together, a relatively smooth, easily applied mass is obtained which can be inserted in the usual manner into prepared cavities and which will harden there within approximately three minutes. The filling can then be finished and polished.

EXAMPLE 7

(Comparative Test)

The process described in Example 6 is repeated and five cylindrical forms are prepared for each paste with the dimensions as listed in Example 4.

For comparison purposes, two pastes are prepared with the same composition as in Example 6 except that the dimethacrylate disclosed in German Pat. No. 1,921,869 and listed in Example 5 above, is substituted for the T-dimethacrylate. Cylindrical forms are prepared in the identical manner for each composition. After 24-hour storage at 36° C, the following average values for compressive strength are found:

| | |
|---|---|
| Pastes based on T-dimethacrylate | 4,050 kg/cm$^2$ |
| Pastes according to the present state of the art | 2,630 kg/cm$^2$ |

EXAMPLE 8

(Paste/paste preparation for tooth fillings)

Two pastes (denominated "A" and "B") are prepared by kneading together the following:

Paste A)
- 1.8 grams of N,N-bis-hydroxyethyl-3,5-di-t-butylaniline, dissolved in 300 grams of T-diacrylate
- 1.8 grams of amorphous, silanized SiO$_2$ of an average primary particle size of 12 mµ and
- 990 grams of silanized quartz powder (<60 µm), tinted to match the tooth color, Paste B)
- 300 grams of T-diacrylate
- 1.8 grams of SiO$_2$ as used in Paste A
- 990 grams of silanized quartz powder (<60 µm), tinted to match the tooth color and containing 6.0 grams of p-chlorobenzoyl peroxide.

When equal parts of the two pastes are mixed together, the processing span (counting from the beginning of the intermixing) is approximately 1 minute and 50 seconds at 24° C. The hardening process is then checked by means of a rheometer and it is thus determined that the mass has substantially solidified and hardened after an additional 25 seconds.

The comparative paste/paste mixture prepared in Example 7 in accordance with the present state of art requires, at the identical processing span and temperature, approximately 90 seconds for the subsequent hardening which shows that the compositions prepared in accordance with the present invention harden more rapidly, allowing an earlier finishing operation, thus advantageously reducing the waiting time for the dentist and patient for the completion of a filling.

EXAMPLE 9

(Combination of T-diacrylate of the present invention with a dimethacrylate prepared in accordance with the present state of the art)

Two pastes (denominated "A" and "B") are prepared. Paste A corresponds to Paste A of Example 8. Paste B (the peroxide-containing paste) corresponds to Paste B of Example 8 except that the dimethacrylate of 2,2-bis-[p-(γ-hydroxypropoxy-)phenyl]-propane disclosed by German Pat. No. 1,921,869 is utilized in place of the T-diacrylate.

The pastes are mixed in a ratio (by weight) of 1 : 1 and the compressive strength is determined by means of test specimen as described in Example 4. The average value so measured is 3,640 kg/cm$^2$ which is definitely higher than for standard preparations for the filling of teeth even though only one of the components was prepared on the basis of a substance proposed by the present invention.

EXAMPLE 10

(Preparation for tooth fillings in a pre-apportioned form)

Mixing containers as proposed by the published German application 23 24 296 are used. 96 mgrams of T-diacrylate, containing 0.3% of N,N-bis-hydroxyethyl-3,5-di-t-butylaniline are fused as individual units into foil cushions which consists of aluminum lined with polypropylene. The cushions are fastened under a clasp which embraces the main pocket. The main pocket is filled in each case with 330 mgrams of silanized quartz powder (<$a\mu$m), tinted to match the tooth color and containing 0.2% of p-chlorobenzoyl peroxide.

Pressure is then exerted upon the clasp by a suitable device, causing the foil cushion to burst and its contents to enter the main pocket. The container is then placed into a mechanical shaker, mixed and the resulting mixture is inserted directly into a properly prepared tooth cavity. The processing span is approximately 2 minutes at 23° C, and the hardening is substantially completed after another 1 minute.

EXAMPLE 11

(Comparative abrasion tests)

Paste/paste preparations based on T-dimethacrylate as defined in Example 6 and based on the diester disclosed by German Pat. No. 1,921,869 as defined in Example 7, in each case mixed in a 1 : 1 ratio, are prepared.

In order to test the abrasion resistance of these compositions, round test specimen of 20 mm diameter and 1.5 mm thickness are produced in properly formed metallic molds. Their weight is then determined. The specimen are then contacted for 24 hours by a suspension of calcium carbonate in water (weight ratio of 1 : 1.5) and by motor-driven standardized circular brushes of 10 mm diameter rotating at 60 rpm. The load of the brushes is 500 grams. After drying, the loss of weight of the specimen is determined with the following results:

|  | Abrasion Loss |
|---|---|
| Preparation based on T-dimethacrylate | 0.3 mgram |
| Preparation according to the state of the art | 2.7 mgram |

The already low abrasion of the preparation according to the state of art is reduced still further by use of a substance proposed by the invention, approximately by a power of ten, thus again proving the superiority of the novel preparation of the present invention for the filling of teeth.

EXAMPLE 12

(Tooth-filling material which is polymerizable by ultra-violet light)

A composition for tooth filling which can be hardened by ultra-violet light and which is ready for use is prepared by first mixing 100 grams of T-dimethacrylate with 0.5 gram of α-(2-cyanethyl)-benzoinmethylether and kneading the resulting mixture with 5 grams of the SiO$_2$ powder defined in Example 8 and 345 grams of silanized quartz powder (particle size <60 $\mu$m), tinted to match the color of the tooth.

When irradiated by a commercially available UV-polymerization unit with a 70 mW output, a mass with a thickness of 2 mm hardens after six seconds.

EXAMPLE 13

(Tooth-filling material which is polymerizable by visible light)

By kneading together of 20 grams of T-acrylate, 88 grams of silanized quartz powder (<60 $\mu$m), tinted to match the tooth color, 1 gram of SiO$_2$ as defined in Example 8, 0.8 gram of methacrylic acid-(N,N-dimethylamino)-ethylester and 4 mgrams of phenanthrenequinone, there is obtained a preparation for the filling of teeth which is ready for use and which will remain in easily workable condition in diffused daylight or under a standard 65-watt bulb for more than 5 minutes. Hardening is accomplished by irradiation with a halogen-projector lamp (12 V, 75 watt) and cold-light mirror. Light with wavelengths <400 nm is screened off by a filter. After an irradiation time of 20 seconds, the mass with a thickness of 2.5 mm is hardened.

EXAMPLE 14

(Sealing composition for dental-enamel fissures)

Two solutions are prepared based on T-dimethacrylate, with one solution containing 0.45% of N,N-bishydroxyethyl-p-toluidine and the other 0.4% of chlorobenzoyl peroxide. Equal portions of these solutions are then mixed together.

The sealing composition so produced is applied to the enamel of the tooth after it has been slightly etched in the usual manner with a 30% solution of phosphoric acid. Hardening begins after approximately 1 minute and is substantially complete after approximately 2 minutes, resulting in a seal that is smooth and resistant to abrasion.

EXAMPLE 15

(Coating preparations for tooth fillings which can be hardened by ultra-violet light including the combination of known diacrylates with substances proposed by the invention)

The various diacrylates listed in the Table below are admixed in the parts by weight indicated therein. 0.3% by weight of benzildimethylketal and 0.5% by weight of didecylphenylphosphite are dissolved in each mixture and 35% by weight of silanized, pyro-SiO$_2$ are added and uniformly distributed. The coating compositions so obtained can be spread easily.

The compressive strength of coatings based on these compositions is measured by the use of specimen having the dimensions 2 × 2 × 4 mm. Hardening is accomplished by irradiation with a commercially available UV-polymerization unit with an output of 70 mW. The values obtained are shown in the Table below.

| Composition (in parts by weight) | | | | |
|---|---|---|---|---|
| T-diacrylate | T-dimeth-acrylate | hexane-diol-dimeth-acrylate | hexane-dioldi-acrylate | Compressive strength (kg/cm$^2$) |
| 100 | 0 | 0 | 0 | 3,940 |
| 0 | 100 | 0 | 0 | 3,900 |
| 50 | 0 | 50 | 0 | 5,750 |
| 0 | 50 | 50 | 0 | 6,030 |
| 0 | 66.7 | 33.3 | 0 | 5,300 |
| 50 | 0 | 0 | 50 | 5,200 |

Surprisingly, combinations of the diester compounds proposed by the present invention with the hexanedioldi(meth)-acrylate in weight ratios ranging from 1 : 1 to 2 : 1 show substantially greater compressive strength values than when only the substances proposed by the invention are used. The use of coating composition based on the pure hexanedioldi(meth)acrylate without the admixture of T-diacrylate and/or T-dimethacrylate is not feasible in practice due to the enormous brittleness of the hardened mass. The combination with the T-diester compound in the manner proposed by the present invention reduces this brittleness and, at the same time, improves the compressive strength of the hardened composition.

EXAMPLE 16

(Manufacture of a jacket crown)

A paste is made of T-acrylate-methacrylate (mixed esters prepared in accordance with Example 3) and solid polymethylmethacrylate in pearl form, commercially available in various tooth color schemes in a ratio of 2 : 3. The several color shades of the pearl polymerization product were previously mixed in each case with 0.4% of lauroyl peroxide.

Onto an isolated tooth stump die, there are deposited layers of the necessary color shades to match the color of the natural teeth. Each layer is briefly heated to approximately 140° C by a flow of hot air. After the completion of the crown, polymerization is completed for 10 minutes at 150° C. The crown so obtained is very highly resistant to abrasion and appears very close to the natural teeth.

EXAMPLE 17

(Veneering a noble metal bridge)

T-dimethylacrylate and polymethylmethacrylate-pearl polymerization product, tinted to match the color of the teeth and previously impregnated with 0.4% of lauroyl peroxide are used. as in Example 16, by making the two components into a paste, at a ratio of 2 : 3.

Onto the frame of the bridge (which is provided in the usual manner with retentions) the individual color shades are applied in layers at the front side, with each layer hardened as described in Example 16.

The veneers are distinguished by their excellent stability and especially by a high resistance to abrasion throughout their use inside the mouth. In addition, their appearance is faultless.

The principles, preferred embodiments and modes of operation of the present invention have been described in the foregoing specification. The invention which is intended to be protected herein, however, is not to be construed as limited to the particular forms disclosed, since these are to be regarded as illustrative rather than restrictive. Variations and changes may be made by those skilled in the art without departing from the spirit of the invention.

We claim:

1. A dental composition, especially for tooth fillings and dentures, including at least two components, one component comprising a polymerizable diacrylic acid ester selected from the group consisting of the diacrylic acid ester or dimethacrylic acid ester of bishydroxymethylthricyclo [5.2.1.0$^{2,6}$]-decane and mixtures thereof, the other component comprising a radical-forming substance.

2. The dental composition of claim 1, wherein said composition further includes at least one of fillers, stabilizers and pigments.

3. The dental composition of claim 1, wherein said composition further includes other polymerizable monofunctional or difunctional acrylic or methacrylic acid esters.

4. The dental composition of claim 3, wherein said other polymerizable diacrylic acid esters include the acrylic acid or methacrylic acid esters of at least one compound selected from hexanediol; 2,2 bis-[p-(hydroxyethoxy-)phenyl]-propane; and 2,2 bis-[p-(γ-hydroxypropoxy-)phenyl]-propane.

5. The dental composition of claim 3, wherein at least 20% of said polymerizable diacrylic acid esters are esters of said bishydroxymethyltricyclo[5.2.1.0$^{2,6}$]-decane.

6. The dental composition of claim 1, wherein said radical-forming substance is an oxidation-reduction system.

7. The dental composition of claim 1, wherein said composition further includes an initiator for photopolymerization.

8. The dental composition of claim 1, wherein said components are each liquid or in a liquid form in combination with another liquid component.

9. The dental composition of claim 1, wherein at least one of said components is in a paste form in combination with a filler.

10. The dental composition of claim 1, wherein both of said components are in paste form.

11. In a method for forming dental fillings and prosthetic dental applicances in which a polymerizable diacrylic or dimethacrylic acid ester is polymerized to form a hardened product, the improvement wherein at least 20 percent of said polymerizable ester is the ester of bishydroxymethyltricyclo [5.2.1.0$^{2,6}$]-decane.

12. An improved dental composition having shortened hardening time and after hardening increased compressive strength and abrasion resistance comprising a polymerizable acrylic or methacrylic acid ester or diester and a radical-forming compound, at least 20 percent of the polymerizable ester being the diacrylic or dimethacrylic acid ester of bishydroxymethyltricyclo [5.2.1.0$^{2,6}$]-decane.

* * * * *

UNITED STATES PATENT AND TRADEMARK OFFICE
CERTIFICATE OF CORRECTION

PATENT NO. : 4,131,729

DATED : December 26, 1978

INVENTOR(S) : Werner SCHMITT et al

It is certified that error appears in the above-identified patent and that said Letters Patent are hereby corrected as shown below:

In the Title Page, in the Title, line 3, delete "POLYMERS".

Column 1, line 3, delete "POLYMERS".

Column 2, delete the formula appearing between lines 47 and 54 and insert therefor the following formula:

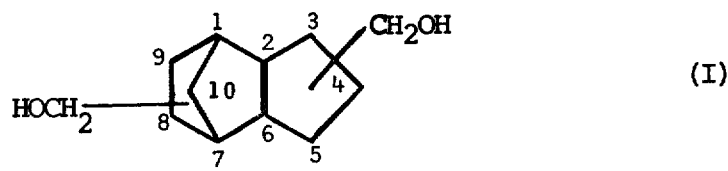

Column 3, line 24, delete "There" and insert therefor --These--.

Column 4, line 34, delete "polymerizations" and insert therefor --polymerization--.

Column 7, line 58, after "2" (second occurrence) delete the comma (,);

Column 8, line 13, delete "T-dimethylacrylate" and insert therefor --T-dimethacrylate--.

Column 9, line 49, delete "(< αμm)" and insert therefor --(< 60 μm)--.

UNITED STATES PATENT AND TRADEMARK OFFICE
CERTIFICATE OF CORRECTION

PATENT NO. : 4,131,729
DATED : December 26, 1978
INVENTOR(S) : Werner SCHMITT et al It is certified that error appears in the above-identified patent and that said Letters Patent are hereby corrected as shown below:

Column 11, line 41, after "of" insert --a--.

Column 12, line 5, delete "T-dimethylacrylate" and insert therefor --T-dimethacrylate--.

Column 12, line 57, delete "further".

Column 12, line 68, delete "applicances" and insert therefor --appliances--.

Signed and Sealed this

Twentieth Day of November 1979

[SEAL]

Attest:

RUTH C. MASON
Attesting Officer

LUTRELLE F. PARKER
Acting Commissioner of Patents and Trademarks